(12) United States Patent
Khan et al.

(10) Patent No.: US 9,169,280 B2
(45) Date of Patent: Oct. 27, 2015

(54) METHODS FOR THE SYNTHESIS OF PLASMALOGENS AND PLASMALOGEN DERIVATIVES, AND THERAPEUTIC USES THEREOF

(71) Applicant: PHENOMENOME DISCOVERIES INC., Saskatchewan (CA)

(72) Inventors: M. Amin Khan, Morgan Hill, CA (US); Paul L. Wood, Harrogate, TN (US); Dayan Goodenowe, Saskatchewan (CA)

(73) Assignee: PHENOMENOME DISCOVERIES INC., Saskatoon, Saskatchewan (CA)

( * ) Notice: Subject to any disclaimer, the term of this patent is extended or adjusted under 35 U.S.C. 154(b) by 0 days.

(21) Appl. No.: 14/359,098

(22) PCT Filed: Nov. 16, 2012

(86) PCT No.: PCT/CA2012/001064
§ 371 (c)(1),
(2) Date: May 17, 2014

(87) PCT Pub. No.: WO2013/071418
PCT Pub. Date: May 23, 2013

(65) Prior Publication Data
US 2014/0296187 A1    Oct. 2, 2014

Related U.S. Application Data

(60) Provisional application No. 61/561,222, filed on Nov. 17, 2011.

(51) Int. Cl.
*C07F 9/6584* (2006.01)
*C07F 9/09* (2006.01)
*C07F 9/10* (2006.01)

(52) U.S. Cl.
CPC .............. *C07F 9/65844* (2013.01); *C07F 9/09* (2013.01); *C07F 9/103* (2013.01)

(58) Field of Classification Search
CPC ......... C07F 9/65844; C07F 9/09; C07F 9/103
See application file for complete search history.

(56) References Cited

U.S. PATENT DOCUMENTS 4,613,621 A    9/1986  Horrmann

OTHER PUBLICATIONS

Farooqui et al. "Plasmalogens: Workhorse Lipids of Membranes in Normal and Injured Neurons and Glia" The Neuroscientist, 2001, pp. 232-245.*
Office Action for Canadian Patent Application No. 2,812,178 (mailed Jul. 31, 2013).
Office Action for Canadian Patent Application No. 2,812,178 (mailed Nov. 27, 2013).

Brites et al., "Functions and Biosynthesis of Plasmalogens in Health and Disease," Biochimica et Biophysica Acta 1636:219-231 (2004).
Grimm et al., "Plasmalogen Synthesis is Regulated via Alkyl-Dihydroxyacetonephosphate-Synthase by Amyloid Precursor Protein Processing and is Affected in Alzheimer's Disease," J. Neurochem. 116:916-925 (2011).
Farooqui et al., "Membrane Phospholipid Alterations in Alzheimer's Disease: Deficiency of Ethanolamine Plasmalogens," Neurochem. Res. 22(4):523-527 (1997).
Wood et al., "Plasmalogen Deficit: a New and Testable Hypothesis for the Etiology of Alzheimer's Disease," in Alzheimer's Disease Pathogenesis-Core Concepts, Shifting Paradigms and Therapeutic Targets, InTech, pp. 561-588 (2011).
Gorgas et al., "The Ether Lipid-Deficient Mouse: Tracking Down Plasmalogen Functions," Biochimica et Biophysica Acta 1762:1511-1526 (2006).
Van Den Bossche et al., "Improved Plasmalogen Synthesis Using Organobarium Intermediates," J. Org. Chem. 72(13):5005-5007 (2007).
International search report and written opinion for corresponding application No. PCT/CA2012/001064, mailed 19 Feb. 2013.
Nishimukai et al., "Ingestion of Plasmalogen Markedly Increased Plasmalogen Levels of Blood Plasma in Rats," Lipids 38(12):1227-1235 (2003).
Shin et al., "Direct Synthesis of Plasmenylcholine from Allyl-Substituted Glycerols," J. Org. Chem. 68:6760-6766 (2003).
Farooqui et al., "Plasmalogens: Workhorse Lipids of Membranes in Normal and Injured Neurons and Glia," Neuroscientist 7(3):232-245 (2001).

* cited by examiner

*Primary Examiner* — Joseph Kosack
(74) *Attorney, Agent, or Firm* — LeClairRyan, a Professional Corporation

(57) ABSTRACT

A method for preparing plasmalogens and derivatives thereof represented by Formula B, wherein R1 and R2 are similar or different, derived from fatty acids; R3 is selected from hydrogen and small alkyl groups. The synthetic route involves production of novel cyclic plasmalogen precursors of Formula A and their conversion to plasmalogens and plasmalogen derivatives of Formula B. Also disclosed is the therapeutic use of plasmalogens and derivatives thereof as produced by the synthetic route of the present invention.

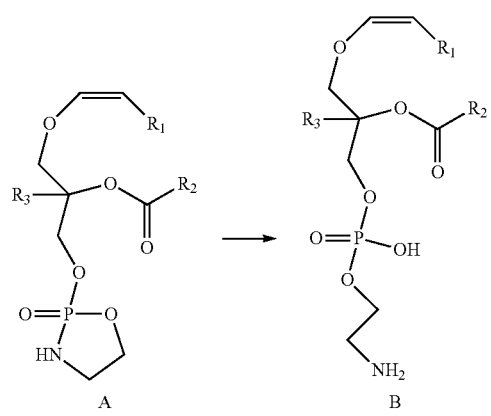

39 Claims, No Drawings

METHODS FOR THE SYNTHESIS OF PLASMALOGENS AND PLASMALOGEN DERIVATIVES, AND THERAPEUTIC USES THEREOF

This application is a national stage application under 35 U.S.C. §371 of PCT Application No. PCT/CA2012/001064, filed 16 Nov. 2012, which claims the priority benefit of U.S. Provisional Patent Application Ser. No. 61/561,222, filed 17 Nov. 2011.

FIELD OF INVENTION

The present invention relates to methods for the chemical synthesis of plasmalogens and plasmalogen derivatives. The invention also relates to the therapeutic uses of plasmalogens and plasmalogen derivatives.

BACKGROUND OF THE INVENTION

Plasmalogens are a class of phospholipids characterized by presence of a vinyl-ether-linked alkyl chain at the sn-1 position, an ester-linked long-chain fatty acid at the sn-2 position, and a head group attached to the sn-3 position through a phosphodiester linkage. They are represented by the following general formula:

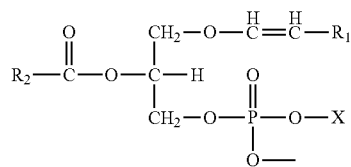

In mammals, the sn-1 position ($R_1$) is typically derived from C16:0, C18:0, or C18:1 fatty alcohols while the sn-2 ($R_2$) position is most commonly occupied by polyunsaturated fatty acids (PUFAs). The head group can have different identities such as ethanolamine, choline etc. Different identities of $R_1$ and $R_2$ and the head group result in different plasmalogen derivatives.

Plasmalogens are found in numerous human tissues, particularly, in the nervous system, the immune system and the cardiovascular system. They represent one fifth of the total phospholipids in the human body. Plasmalogens are thought to have numerous physiological roles. They are an important structural component of the cell membranes, and act as secondary messengers in cell signaling. In fact, almost 30% of the glycerophospholipids in the adult human brain and up to 70% of myelin sheath ethanolamine glycerophospholipids are plasmalogens. They may also be involved in membrane fusion, ion transport, and cholesterol efflux. Plasmalogens may also act as antioxidants, thus protecting cells from oxidative stress (Plasmalogens: Workhorse Lipids of Membranes in Normal and Injured Neurons and Glia. Akhlaq A. Farooqi, Lloyd A. Horrocks; Neuroscientist. 2001 June; 7(3): 232-45).

Apart from their normal physiological roles which are still being elucidated, plasmalogens are also implicated in different human diseases (Functions and biosynthesis of plasmalogens in health and diseases, Pedro Brites, Hans R Waterham, Ronald J. A Wanders; Biochim Biophys Acta. 2004 March 22; 1636(2-3):219-31). In particular, altered levels of tissue plasmalogens has been associated with Zellweger syndrome, rhizomelic chondrodysplasia punctata, Alzheimer's disease, Down syndrome, and Niemann-Pick type C disease etc. (The ether lipid-deficient mouse: tracking down plasmalogen functions. Gorgas K, Teigler A, Komljenovic D, Just W W., Biochim Biophys Acta. 2006 December; 1763(12):1511-26).

A number of reports have been published demonstrating reduced levels of brain plasmalogens in Alzheimer's disease (Plasmalogen synthesis is regulated via alkyl-dihydroxyacetonephosphate-synthase by amyloid precursor protein processing and is affected in Alzheimer's disease, Grimm M O, Kuchenbecker J, Rothhaar T L, Grösgen S, Hundsdörfer B, Burg V K, Friess P, Müller U, Grimm H S, Riemenschneider M, Hartmann T., J Neurochem. 2011 March; 116(5):916-25; Membrane phospholipid alterations in Alzheimer's disease: deficiency of ethanolamine plasmalogens, Farooqui A A, Rapoport S I, Horrocks L A, Neurochem Res. 1997 April; 22(4):523-7.)

Administering plasmalogens so as to overcome the deficit has been postulated as a treatment for Alzheimer's disease (Plasmalogen Deficit: A New and Testable Hypothesis for the Etiology of Alzheimer's Disease, Paul L. Wood, M. Amin Khan, Rishikesh Mankidy, Tara Smith and Dayan B. Goodenowe, Alzheimer's Disease Pathogenesis-Core Concepts, Shifting Paradigms and Therapeutic Targets, Pg. 561-588).

For this therapy to be practical, a source of plasmalogens is needed. Plasmalogens can be extracted from sources such as bovine, mammalian or fish brain and spinal cord, hen egg phospholipids etc. (Ingestion of plasmalogen markedly increased plasmalogen levels of blood plasma in rats, Megumi Nishimukai, Takuya Wakisaka and Hiroshi Hara, LIPIDS Volume 38, Number 12, 1227-1235; U.S. Pat. No. 4,613,621). However, the extracts are usually contaminated with other phospholipids, are difficult to make, and the procedures are costly. Plasmalogens can also be produced through biosynthetic routes, but again problems arise from the need for extensive purification and the use of costly procedures.

Chemical synthesis of plasmalogens can serve to solve the above-mentioned problems. Several approaches have been tried to chemically synthesize plasmalogens (Direct Synthesis of Plasmenylcholine from Allyl-Substituted Glycerols, Junhwa Shin and David H. Thompson, J. Org. Chem., 2003, 68 (17), pp 6760-6766; Improved Plasmalogen Synthesis Using Organobarium Intermediates, Jeroen Van den Bossche, Junhwa Shin,† and David H. Thompson, J. Org. Chem., 2007, 72 (13), pp 5005-5007). However, most of the existing chemical synthesis processes face problems due to the sensitivity of the vinyl-ether bond to acidic conditions, as well as oxidative conditions. Further, there is a difficulty in generating the Z—O-alkenyl functionality stereoselectively.

SUMMARY OF THE INVENTION

To address these and other problems associated with the preparation and synthesis of plasmalogens, this disclosure aims to provide an improved synthetic method.

In certain embodiments, the method for chemically synthesizing plasmalogens described herein may have improved efficiency over other known methods.

In one aspect of the invention, a process is provided for preparing a compound represented by Formula A:

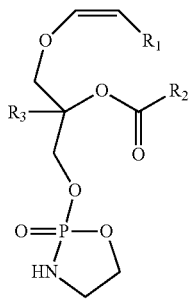

Formula A wherein $R_1$ and $R_2$ are the same or different saturated, unsaturated, or polyunsaturated hydrocarbon chains, and optionally derived from fatty acids; and $R_3$ is hydrogen or a lower alkyl group.

In certain non-limiting embodiments, $R_1$, $R_2$ or both $R_1$ and $R_2$ are $C_1$-$C_{28}$ alkyl chains comprising up to 6 double bonds. For instance, without wishing to be limiting, $R_1$ can be a $C_1$-$C_{20}$ alkyl group, more preferably a $C_{14}$ alkyl group. In other non-limiting embodiments, $R_2$ is a $C_1$-$C_{28}$ alkenyl group, more preferably a $C_{21}$ alkenyl group with 1 to 6 double bonds. In further non-limiting embodiments, $R_3$ is a $C_1$-$C_3$ alkyl group, such as but not limited to methyl, ethyl and propyl.

In this process, the solketel represented by Formula 1:

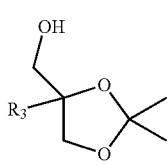

Formula 1 is coupled with an allyl halide, such as but not limited to an allyl bromide, in the presence of NaH to produce a compound represented by Formula 2:

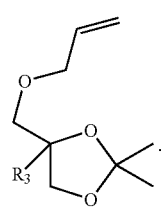

Formula 2

In certain non-limiting embodiments, the compound of Formula 2 is obtained with a yield of up to about 88%.

The ketal group present in the compound represented by Formula 2 is then deprotected using acidic conditions to produce a compound represented by Formula 3:

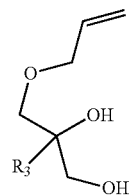

Formula 3

In certain non-limiting embodiments, the compound of Formula 3 is obtained with a yield of up to about 97%.

The diol present in the compound represented by Formula 3 is then protected to produce a compound represented by Formula (iv):

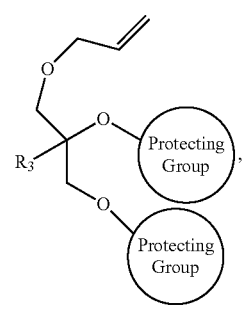

Formula (iv)

for instance, but without limiting, to embodiments whereby the diol is protected with tert-butyldimethylsilyl (TBS) groups to obtain a compound of Formula 4:

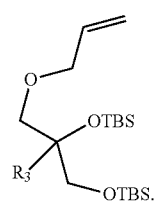

Formula 4

In certain non-limiting embodiments, the compound of Formula 4 is obtained with a yield of up to about 84%.

The compound represented by Formula (iv) is then reacted with a compound as represented by the formula $XR_1$ to produce a compound represented by Formula (v):

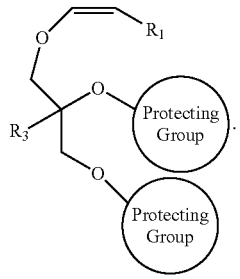

Formula (v)

wherein $R_1$ is as defined above and X is a halogen. In non-limiting embodiments, X can be Cl, Br, F or I. In a further non-limiting embodiment, the compound of Formula 4 can be used to obtain the compound of Formula 5:

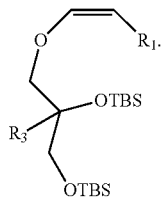

Formula 5

In certain non-limiting embodiments, the compound of Formula 5 is obtained with a yield of up to about 37%.

The ether groups present in the compound represented by Formula 5 are then deprotected to produce a compound represented by Formula 6:

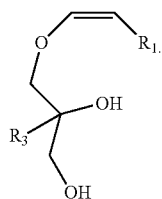

Formula 6

In certain non-limiting embodiments, the compound of Formula 6 is obtained with a yield of up to about 100%.

The primary alcohol present in the compound represented by Formula 6 is then protected to produce a compound represented by Formula (vii):

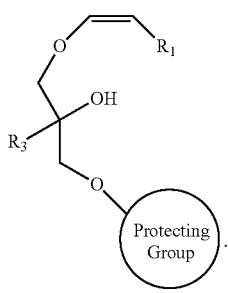

Formula (vii)

For instance, but without being limiting, the primary alcohol can be protected with a tert-butyldimethylsilyl (TBS) group to obtain a compound of Formula 7:

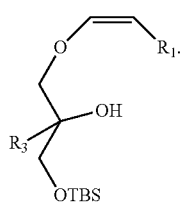

Formula 7

In certain non-limiting embodiments, the compound of Formula 7 is obtained with a yield of up to about 74%.

The compound represented by Formula (vii) is then esterified with a fatty acid represented by $R_2$—COOH to produce a compound represented by Formula (viii):

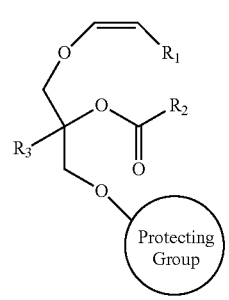

Formula (viii)

wherein $R_2$ is as defined above. In an embodiment, yet without wishing to be limiting, the compound of Formula 7 can be used to obtain the compound of Formula 8:

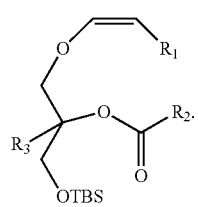

Formula 8

In certain non-limiting embodiments, the compound of Formula 8 is obtained with a yield of up to about 73%.

The ether present in the compound represented by Formula (viii) or, in certain embodiments the compound of Formula 8, is then deprotected to produce a compound represented by Formula 9:

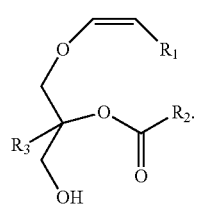

Formula 9

In certain non-limiting embodiments, the compound of Formula 9 is obtained with a yield of up to about 95%.

Finally, the compound of Formula 9 is reacted in two steps with $POCl_3$, $Et_3N$ and ethanolamine to produce the compound represented by Formula A.

In certain non-limiting embodiments, the compound of Formula A can be obtained with a yield of up to about 26%.

In a preferred embodiment, the fatty acid ($R_2$—COOH) is docosahexanoic acid (DHA).

In another preferred embodiment, the compound of the formula $XR_1$ is iodotridecane.

In yet another preferred embodiment, the protection reactions to produce the compounds of Formula 4 and Formula 7 are carried out with tert-butyldimethylsilyl chloride (TBDMSCl).

In a further preferred embodiment, the deprotection reactions to produce the compound of Formula 6 and Formula 9 are carried out in the presence of tetrahydrofuran (THF) and tetra-n-butylammonium fluoride (TBAF).

In yet another preferred embodiment, the fatty acid ($R_2$—COOH) is DHA, and the compound of the formula $XR_1$ is iodotridecane, and the compound produced is as represented in Formula A':

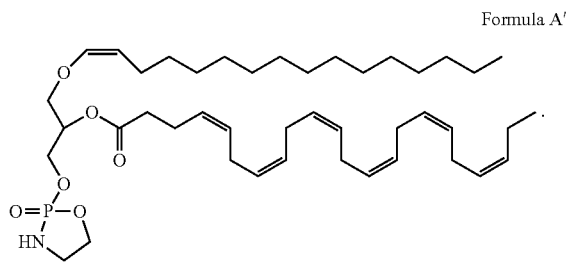 [SMILES: CC/C=C\C/C=C\C/C=C\C/C=C\C/C=C\C/C=C\CCC(=O)OC(CO/C=C\CCCCCCCCCCCCCC)COP1(=O)NCCO1]

Formula A'

In another aspect of the invention, a process is provided for production of a compound represented by Formula B:

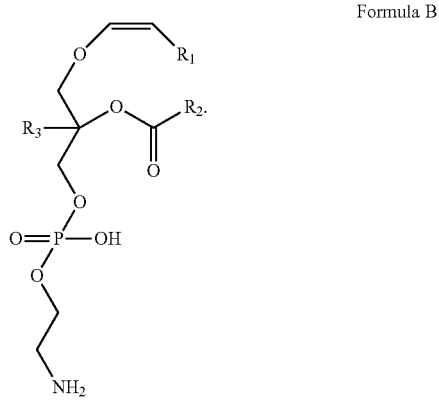

Formula B wherein $R_1$, $R_2$ and $R_3$ are as described above.

In the process, the compound of Formula A as described above is converted to a compound of Formula B in the presence of water and tetrahydrofuran (THF).

In certain embodiments, the compound of Formula A may be prepared according to methods as described above. In addition, according to a preferred embodiment, the compound of Formula A' as described above may accordingly be converted to a compound as represented by Formula B':

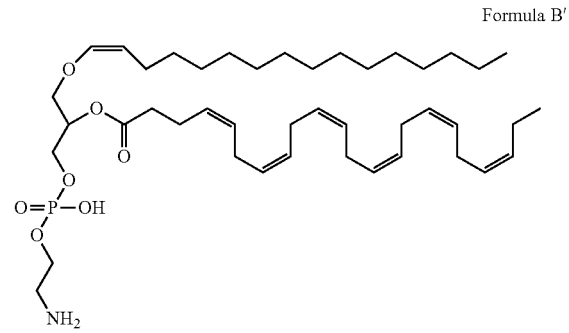 [SMILES: CC/C=C\C/C=C\C/C=C\C/C=C\C/C=C\C/C=C\CCC(=O)OC(CO/C=C\CCCCCCCCCCCCCC)COP(=O)(O)OCCN]

Formula B' by the above process.

DETAILED DESCRIPTION

The present invention provides cyclic precursors useful in the synthesis of plasmalogens and derivatives thereof, the precursor being represented by the compound of Formula A:

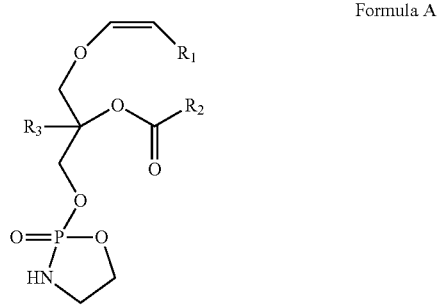

Formula A wherein $R_1$ and $R_2$ are the same or different saturated, unsaturated, or polyunsaturated hydrocarbon chains, and optionally derived from fatty acids; and $R_3$ is hydrogen or a lower alkyl group.

In certain non-limiting embodiments, $R_1$, $R_2$ or both $R_1$ and $R_2$ are $C_1$-$C_{28}$ alkyl chains comprising up to 6 double bonds. For instance, without wishing to be limiting, $R_1$ can be a $C_1$-$C_{20}$ alkyl group, more preferably a $C_{14}$ alkyl group. In other non-limiting embodiments, $R_2$ is a $C_1$-$C_{28}$ alkenyl group, more preferably a $C_{21}$ alkenyl group with 1 to 6 double bonds. In further non-limiting embodiments, $R_3$ is a $C_1$-$C_3$ alkyl group, such as but not limited to methyl, ethyl and propyl.

The present invention also provides a process for preparing cyclic precursors useful in the synthesis of plasmalogens and derivatives thereof, the precursors being represented by compounds of Formula A as described above.

In certain embodiments, yet without wishing to be limiting in any way, these cyclic precursors can provide several advantages for efficient synthesis of plasmalogens. For instance, the polarity and solubility of the cyclic intermediate can increase the ease of purification of the intermediate. The cyclic intermediate is also, in certain embodiments, stable under both chromatographic conditions and under HPLC conditions; and can be hydrolyzed to produce plasmalogens in aqueous media.

The present invention further provides a process for preparing plasmalogens as represented by compounds of Formula B

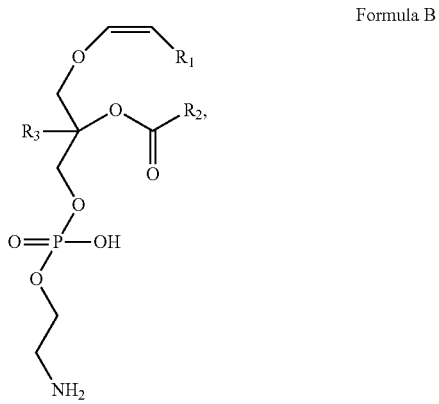

Formula B wherein $R_1$, $R_2$ and $R_3$ are as described above,
from the cyclic precursors as represented by compounds of Formula A.

This synthetic route can, in certain preferred embodiments, yield high purity of plasmalogen, and at reduced cost as compared to other methods through the use of generally abundant and inexpensive reagents. The process also has the advantage that, in certain embodiments, no downstream processing is required. In addition, because a highly pure plasmalogen product can be obtained in certain non-limiting embodiments of the described process, the relative amount of plasmalogen that is needed in the end application(s) is reduced, which can further reduce costs.

It will be appreciated by those skilled in the art that each of the embodiments of the invention described herein may be utilized individually or combined in one or more manners different than the ones disclosed above for the production of plasmalogens. In addition, those skilled in the art will be able to select a suitable temperature in view of the reaction conditions being used, in further embodiments of the invention encompassed herein.

The literature referred to herein establishes knowledge that is available to those with skill in the art. Unless otherwise defined, all technical and scientific terms used herein have the same meaning as commonly understood by one of ordinary skill in the art to which this invention relates. All references cited herein are hereby incorporated by reference to the same extent as if each was specifically and individually incorporated by reference.

Although methods and materials similar or equivalent to those described herein can be used in the practice or testing of the present invention, the preferred methods and materials are described herein. In the case of inconsistencies, the present disclosure, including definitions, will control. In addition, the materials, methods, and examples are illustrative only and are not intended to be limiting.

The term "about" is used herein to mean approximately, in the region of, roughly, or around. When the term "about" is used in conjunction with a numerical range, it modifies that range by extending the boundaries above and below the numerical values set forth. The term "comprises" is used herein to mean "includes, but is not limited to."

The following abbreviations are used throughout the specification:
AcOH: Acetic Acid
DCM: Dichloromethane
DHA: Docosahexanoic Acid
DHP: Dihydropyran
DMAP: 4-Dimethylaminopyridine
DMF: Dimethylformamide
EDC: 1-ethyl-3-(3-dimethylaminopropyl) carbodiimide
EDC.HCl: 1-Ethyl-3-(3-dimethyllaminopropyl)carbodiimide hydrochloride
EtOAc: Ethyl Acetate
Et$_3$N: Triethylamine
HCl: Hydrocholoric Acid
HMPA: Hexamethylphosphoramide
Im: Imidazole
MeOH: Methanol
NaH: Sodium Hydride
NaHCO$_3$: Sodium Carbonate
Na$_2$SO$_4$: Sodium Sulphate
n-BuLi: n-Butyllithium
Pd/C: Palladium on Carbon
POCl$_3$: Phosphoryl Chloride
PPh$_3$: Triphenyl Phosphine
PTSA: p-toluenesulfonic acid
Sec-BuLi: sec-Butyllithium
TBAF: Tetra-n-butylammonium fluoride
TBDMSCl: tert-Butyldimethylsilyl chloride
TEA: Triethanolamine
THF: Tetrahydrofuran
THP: Tetrahydropyran In one embodiment of the invention, cyclic precursors for plasmalogen synthesis represented by compounds of Formula A are provided:

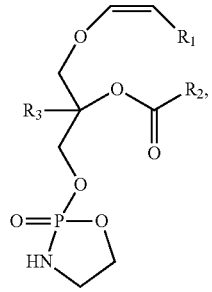

Formula A wherein $R_1$ and $R_2$ are the same or different saturated, unsaturated, or polyunsaturated hydrocarbon chains, and optionally derived from fatty acids; and $R_3$ is hydrogen or a lower alkyl group.

In certain non-limiting embodiments, $R_1$, $R_2$ or both $R_1$ and $R_2$ are $C_1$-$C_{28}$ alkyl chains comprising up to 6 double bonds. For instance, without wishing to be limiting, $R_1$ can be a $C_1$-$C_{20}$ alkyl group, more preferably a $C_{14}$ alkyl group. In other non-limiting embodiments, $R_2$ is a $C_1$-$C_{28}$ alkenyl group, more preferably a $C_{21}$ alkenyl group with 1 to 6 double bonds. In further non-limiting embodiments, $R_3$ is a $C_1$-$C_3$ alkyl group, such as but not limited to methyl, ethyl and propyl.

$R_1$ and $R_2$ can, in certain embodiments, be derived from any saturated, unsaturated or polyunsaturated fatty acids, or from alkyl, alkenyl or alkynyl halides.

In a preferred embodiment, $R_1$ is derived from iodotridecane, $R_2$ is derived from docosahexanoic acid, and $R_3$ is hydrogen such that the compound of Formula A is:

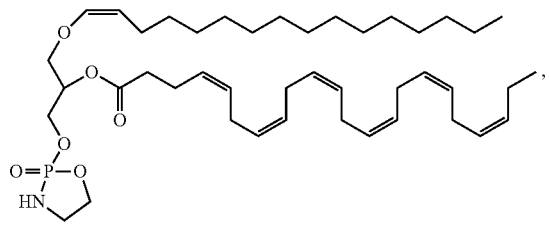

Formula A'

In further non-limiting embodiments, and in addition to iodotridecane, the alkyl halides may alternately be chlorotridecane, bromotridecane, fluorotridecane.

In yet further embodiments, the term "lower alkyl group" may refer to a $C_{1-3}$ alkyl group, preferably a straight chain alkyl group such as methyl, ethyl or propyl.

In another non-limiting embodiment, a 9-step synthetic process is provided for preparing cyclic precursors for plasmalogen synthesis, wherein the cyclic precursors are represented by compounds of Formula A. The synthetic process is depicted in Scheme A:

Scheme A

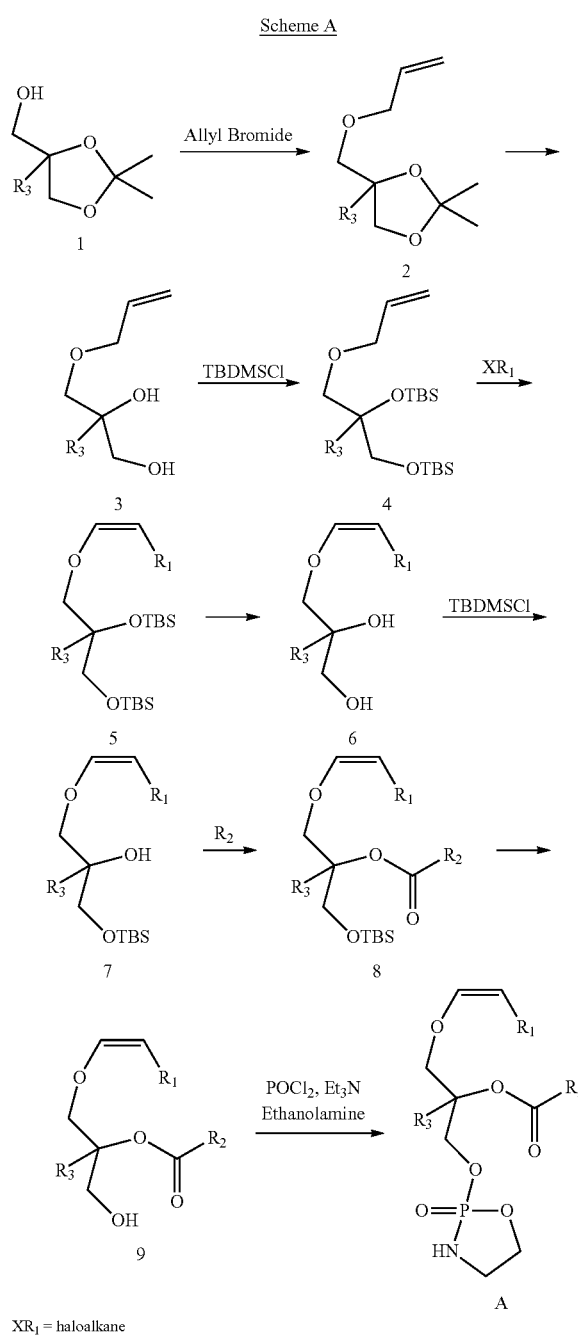

XR₁ = haloalkane

In this synthetic process, the primary alcohol in solketal of Formula 1 is coupled with allyl bromide to produce a compound represented by Formula 2. Ketal in the compound represented by Formula 2 is deprotected to obtain a compound represented by Formula 3. The diol of the compound represented by Formula 3 is protected as a TBDMS ether to obtain a compound represented by Formula 4. The compound represented by Formula 4 is reacted with a haloalkane, preferably yet not limited to iodotridacene, in the presence of sec-BuLi to produce a compound represented by Formula 5. The TBDMS ether in the compound of Formula 5 is deprotected to produce the compound represented by Formula 6. The primary alcohol present in the compound represented by Formula 6 is protected with TDBMS to obtain a compound represented by Formula 7. A fatty acid, preferably but not limited to DHA, is esterified at the sn2 position of the compound represented by Formula 7 in the presence of EDC.HCL/DMAP to produce a compound represented by Formula 8. The compound represented by Formula 8 is deprotected in the presence of excess AcOH to produce a compound represented by Formula 9. A cyclic phosphoethanolamine group is added to the compound represented by Formula 9 to produce a compound represented by Formula A, using a two step protocol, wherein POCl₃ is added to the compound represented by Formula 9 to produce a dichlorophosphate intermediate, which is then quenched with ethanolamine to give the cyclic phosphoethanolamine.

In another non-limiting embodiment, a process is provided for preparing plasmalogens as represented by the compounds of Formula B described herein, using the cyclic precursors as represented by the compounds of Formula A described herein. This process is depicted in Scheme B:

Scheme B

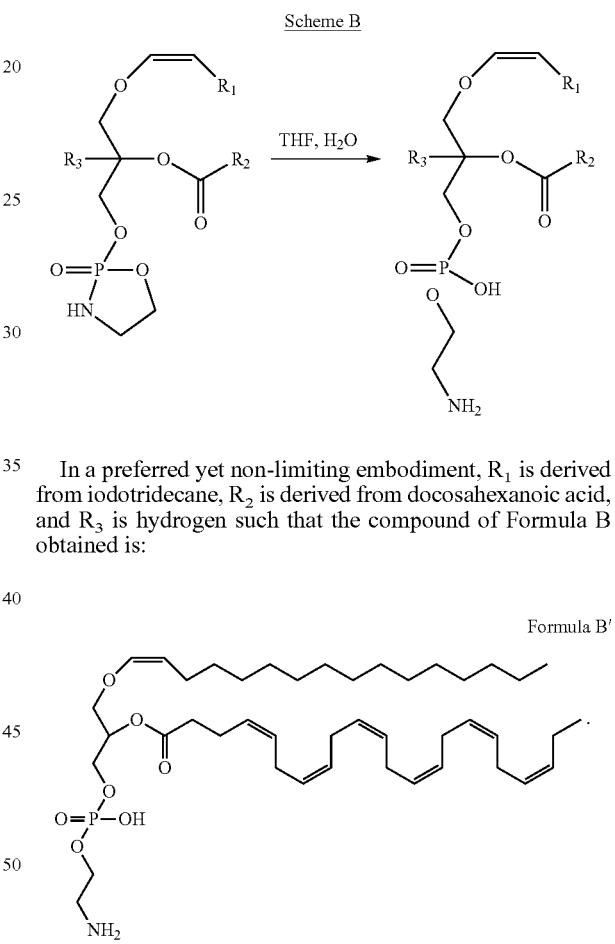

In a preferred yet non-limiting embodiment, $R_1$ is derived from iodotridecane, $R_2$ is derived from docosahexanoic acid, and $R_3$ is hydrogen such that the compound of Formula B obtained is:

Formula B'

This conversion of the cyclic plasmalogen precursor of Formula A to the plasmalogen of Formula B is a single step process and is carried out in aqueous media.

EXAMPLES

The following provides examples of certain preferred embodiments of the synthetic processes described herein for producing the cyclic plasmalogen precursor of Formula A, and the plasmalogen of Formula B.

A non-limiting example of a process for production of the cyclic plasmalogen precursor of Formula A in accordance with a preferred embodiment of the invention is depicted in Scheme C:

Scheme C
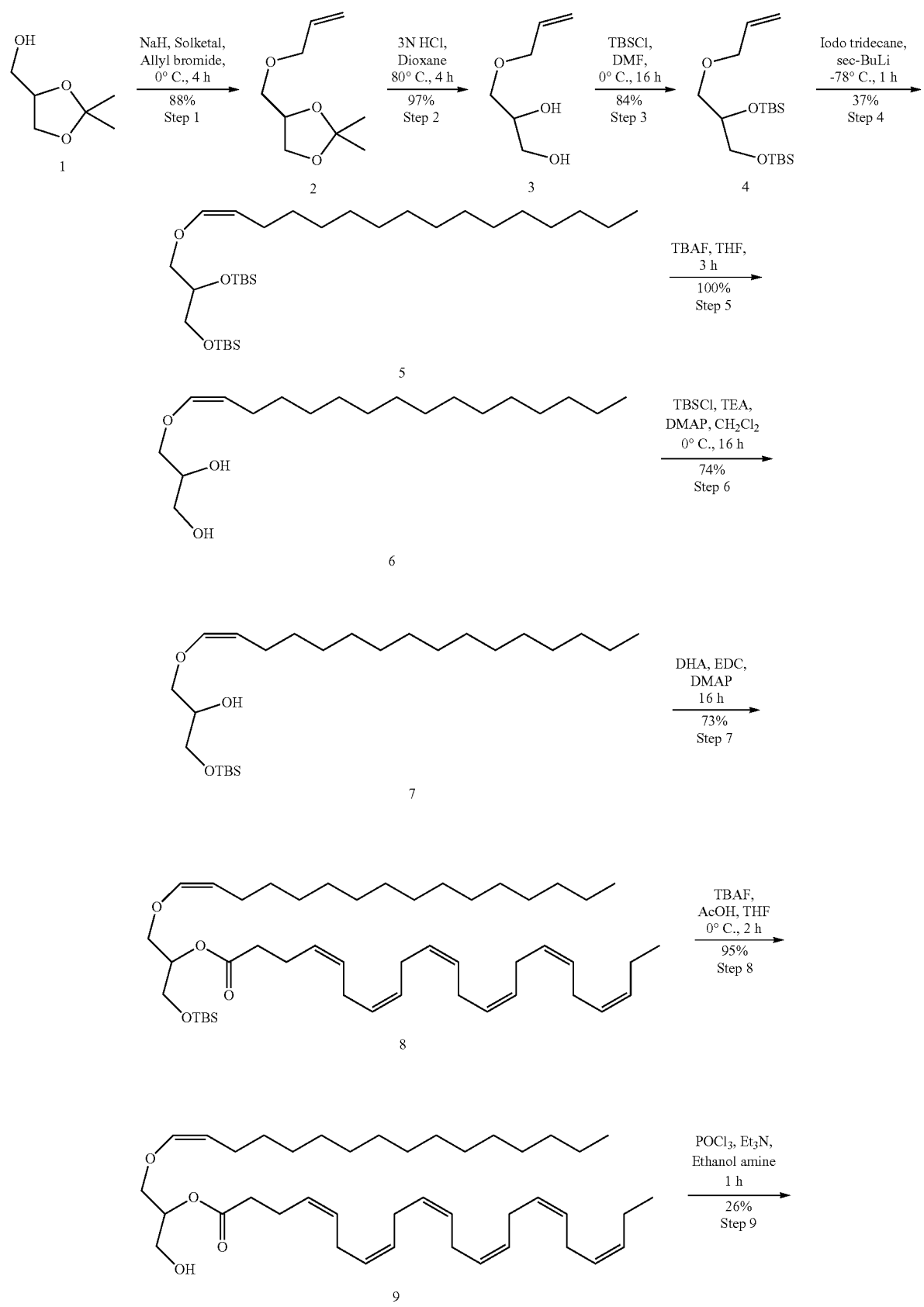

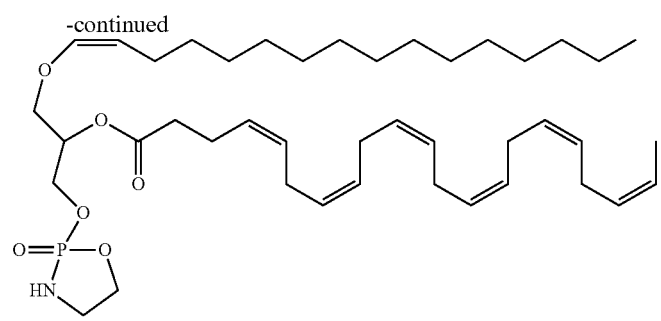

PHE-GLC-10-Cold-Cyclic

A non-limiting example of a process for production of the plasmalogen of Formula B in accordance with a preferred embodiment of the invention is depicted in Scheme D:

DHA/PTSA and resulting in a compound represented by Formula (ii). The reaction scheme involved in this process is as follows:

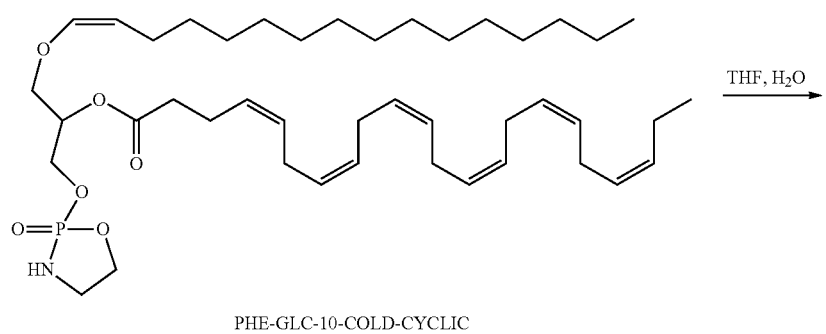

PHE-GLC-10-COLD-CYCLIC

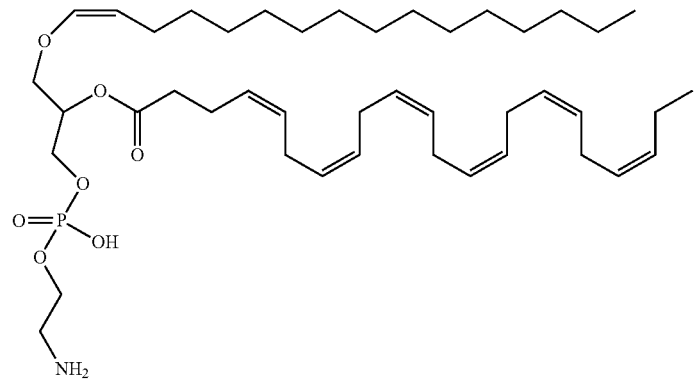

PHE-GLC-10-COLD

Example 1

Synthesis of Iodotridecane

In a preferred embodiment of the invention, iodotridecane is the haloalkane used in the process of synthesizing the plasmalogen precursor. The iodotridecane can be obtained by chemical synthesis. The process for the same is explained in the details below.

Preparation of a Compound Represented by Formula (ii):

In the first step of the synthetic process the primary alcohol present in propargyl alcohol as represented by Formula (i) was protected by ether bond formation, by reacting it with

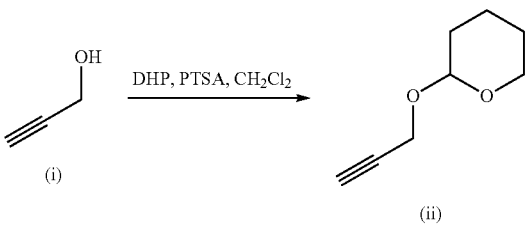

In a non-limiting embodiment, the raw materials used for this process are illustrated in Table 1:

TABLE 1

| S. No. | Name of the Material | Qty. | M. Wt. | mmol | Mole Ratio |
|---|---|---|---|---|---|
| 1. | Propargyl alcohol | 1 g | 56.06 | 16.93 | 1 |
| 2. | Dichloromethane | 15 mL | 84.93 | — | 15 vol. |
| 3. | PTSA | 3 mg | — | 0.16 | 0.009 |
| 4. | DHP | 3 mL | 84.12 | 33.86 | 2 |
| 5. | NaHCO$_3$ | — | 84.01 | — | — |
| 6. | Dichloromethane | 2 × 100 mL | 84.93 | — | 2 × 100 vol. |
| 7. | Water | 2 × 100 mL | 18 | — | 2 × 100 vol. |
| 8. | Brine | 1 × 100 mL | — | — | 100 vol. |

To a solution of propargyl alcohol (1 g, 16.93 mmol) in dichloromethane (15 mL), PTSA (3 mg, 0.16 mmol) and DHP (3 mL, 33.86 mmol) were added and the reaction mixture was stirred at room temperature for 2 h. After completion of starting materials, the reaction mixture was quenched with NaHCO$_3$ and extracted with dichloromethane (100 mL×2), washed with water (100 mL×2), and brine (100 mL×1). The combined organic extracts were evaporated under reduced pressure to obtain the crude product which was purified by column chromatography (100-200 mesh silica gel, eluent 10% EtOAc in hexane) to furnish compound (ii) (2.078 g, 87%) as a light brown liquid.

Preparation of a Compound Represented by Formula (iii):

The compound represented by Formula (ii) was alkylated with iododecane to obtain a compound represented by Formula (iii). The reaction scheme involved in this process is as follows:

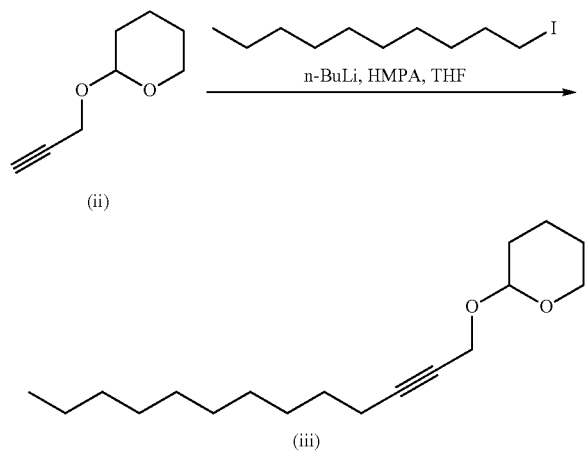

In a non-limiting embodiment, the raw materials used for this process are illustrated in Table 2:

TABLE 2

| S. No. | Name of the Material | Qty. | M. Wt. | mmol | Mole Ratio |
|---|---|---|---|---|---|
| 1. | Compound of Formula (ii) | 2.07 g | 142.76 | 14.5 | 1 |
|  | Iododecane | 3.8 mL | 268.18 | 17.4 | 1.2 |
| 2. | THF | 40 mL | 72.11 | — | 19.32 vol. |
| 3. | HMPA | 3.78 mL | 179.2 | 21.7 | 1.49 |
| 4. | n-BuLi | 7.54 mL | 64.06 | 18.86 | 1.3 |
| 5. | Ethyl acetate | 3 × 30 mL | 88.11 | — | 3 × 14.49 vol. |
| 7. | Water | 25 mL | 18 | — | 12.08 vol. |

TABLE 2-continued

| S. No. | Name of the Material | Qty. | M. Wt. | mmol | Mole Ratio |
|---|---|---|---|---|---|
| 8. | Brine | 25 mL | — | — | 12.08 vol. |
| 9. | Na$_2$SO$_4$, anhydrous | As needed | 142.04 | — | — |

To a solution of compound represented by Formula (ii) (2.07 g, 14.5 mmol) in THF (40 mL), HMPA (3.78 mL, 21.7 mmol) and n-BuLi (2.5 M, 7.54 mL, 18.86 mmol) were added drop wise at −78° C. After 1 hour, iododecane (3.8 mL, 17.4 mmol) in THF was added drop wise at −78° C. and stirred at room temperature for 16 h. After completion of starting materials, the reaction mixture was quenched with ice and extracted with ethyl acetate (30 mL×3), washed with water (25 mL×1), brine (25 mL×1) and dried over anhy. Na$_2$SO$_4$. The combined organic extracts were evaporated under reduced pressure to obtain the crude product which was purified by column chromatography (100-200 mesh silica gel, eluent 10% Dichloromethane in hexane) to furnish compound represented by Formula (iii) (1.94 g, 47%) as a light yellow liquid.

Preparation of a Compound Represented by Formula (iv):

Hydrogenation of the compound represented by Formula (iii) resulted in a compound represented by Formula (iv). The reaction scheme involved in this process is as follows:

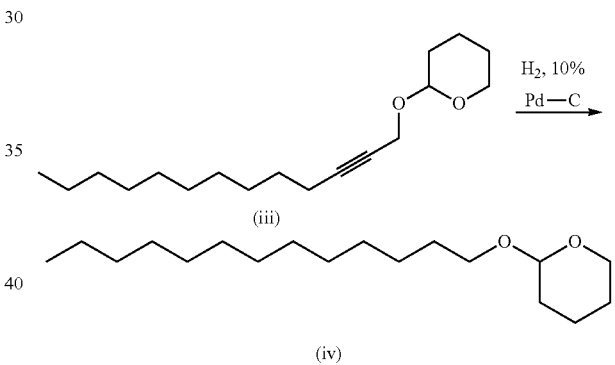

In a non-limiting embodiment, the raw materials used for this process are illustrated in Table 3:

TABLE 3

| S. No. | Name of the Material | Qty. | M. Wt. | mmol | Mole Ratio |
|---|---|---|---|---|---|
| 1. | Compound of Formula (iii) | 870 mg | 284.31 | 3.06 | 1 |
| 2. | Pd/C (10%) | 100 mg | — | — | — |
| 3. | Ethyl acetate | 2 × 30 mL | 88.11 | — | 2 × 9.8 vol. |

To a solution of the compound represented by Formula (iii) (870 mg, 3.06 mmol) in ethyl acetate (10 mL), 10% Pd/C (100 mg) was added and the reaction was stirred under hydrogen atmosphere for 12 h. After completion of starting material, the reaction mass was filtered through a Celite™ pad and washed with ethyl acetate (30 mL×2) twice. The combined organic extracts were evaporated under reduced pressure to obtain the crude product which was purified by column chromatography (100-200 mesh silica gel, 5% ethyl acetate in hexane) to furnish the compound represented by Formula (iv) (800 mg, 90%) as a colorless liquid.

Preparation of a Compound Represented by Formula (v):

THP present in the compound of Formula (iv) was deprotected to produce the compound represented by Formula (v). The reaction scheme involved in this process is as follows:

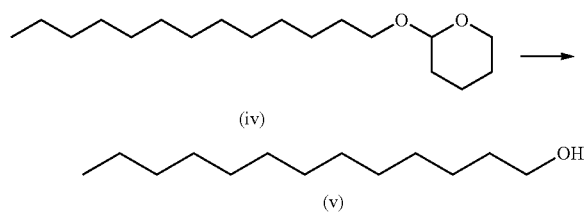

In a non-limiting embodiment, the raw materials used for this process are illustrated in Table 4:

TABLE 4

| S. No. | Name of the Material | Qty. | M. Wt. | mmol | Mole Ratio |
|---|---|---|---|---|---|
| 1. | Compound of Formula (iv) | 1.1 g | 287.96 | 3.82 | 1 |
| 2. | Methanol | 10 mL | 32 | — | 9.09 vol. |
| 3. | PTSA | 65 mg | — | 0.37 | 0.097 |
| 4. | NaHCO$_3$ | — | 84.01 | — | — |
| 5. | Ethyl acetate | 2 × 50 mL | 88.11 | — | 2 × 45.45 vol. |
| 6. | Water | 100 mL | — | — | 90.90 vol. |
| 7. | Brine | 50 mL | — | — | 45.45 vol. |
| 8. | Na$_2$SO$_4$ | As needed | 142.04 | — | — |

To a solution of compound represented by Formula (iv) (1.1 g, 3.82 mmol) in methanol (10 mL), PTSA (65 mg, 0.37 mmol) was added and the reaction was stirred at room temperature for 2 h. After completion of starting material, the reaction mixture was quenched with NaHCO$_3$ and concentrated, extracted with ethyl acetate (50 mL×2) washed with water (100 mL×1), brine (50 mL×1) and dried over Na$_2$SO$_4$. The combined organic extracts were evaporated under reduced pressure to obtain the crude product which was purified by column chromatography (100-200 mesh silica gel, 30% dichloromethane in hexane) to furnish the compound represented by Formula (v) (700 mg, 90%) as a colorless liquid.

Preparation of Iodotridecane:

The compound of Formula (v) was converted to iodotridecane by iodination of the primary alcohol present in the compound of Formula (v). The reaction scheme involved in this process is as follows:

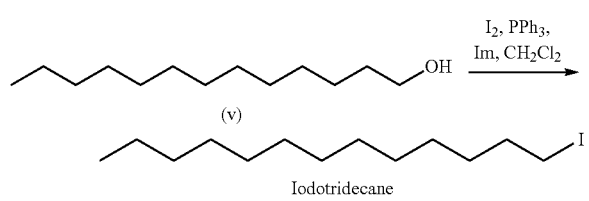

In a non-limiting embodiment, the raw materials used for this process are illustrated in Table 5:

TABLE 5

| S. No. | Name of the Material | Qty. | M. Wt. | mmol | Mole Ratio |
|---|---|---|---|---|---|
| 1. | Compound of Formula (v) | 1.08 g | 203.39 | 5.31 | 1 |
| 2. | I$_2$ | 1.48 g | 253 | 5.84 | 1.1 |
| 3. | Dichloromethane | 20 mL | 84.93 | — | 18.52 vol. |
| 4. | Triphenyl phosphine | 1.53 g | 262.29 | 5.84 | 1.1 |
| 5. | Imidazole | 0.39 g | 68.07 | 5.84 | 1.1 |

To a solution of tridecanol (1.08 g, 5.31 mmol) in dichloromethane (20 mL), triphenyl phosphine (1.53 g, 5.84 mmol) and imidazole (0.39 g, 5.84 mmol) were added and cooled to 0° C. I$_2$ (1.48 g, 5.84 mmol) was added and the reaction mixture was stirred at room temperature for 3 h. After completion of starting materials, the reaction mixture was evaporated and diluted with hexane and passed through a Celite™ pad. The combined organic extracts were evaporated under reduced pressure to obtain the crude product which was purified by column chromatography (100-200 mesh silica gel, eluent hexane) to furnish iodotridecane (1.43 g, 84%) as a low melting solid.

Example 2

Synthesis of a Cyclic Plasmalogen Precursor of Formula a by the 9-Step Chemical Synthetic Process In a preferred embodiment of the invention, a 9-step synthetic process is provided for production of the novel cyclic plasmalogen precursor represented by Formula A wherein R$_1$ is derived from iodotridecane, R$_2$ is derived from docosahexanoic acid and R$_3$ is hydrogen (See Scheme C). Each of the 9-steps in the chemical synthetic process will now be described in detail by way of the following example.

Preparation of a Compound of Formula 2 (4-(allyloxymethyl)-2,2-dimethyl-1,3-dioxolane)

In the first step of the synthetic process, solketal of Formula 1 was coupled to allyl bromide in the presence of NaH to produce a compound of Formula 2. The yield of the compound obtained in this reaction step was 88%. The reaction scheme involved in this process is as follows:

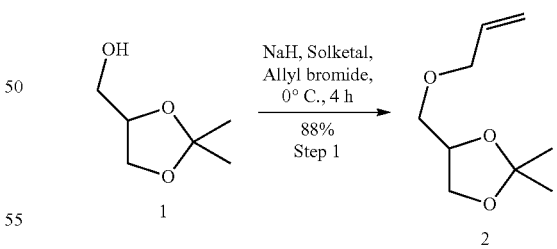

In an exemplary embodiment, the raw materials used for this step are illustrated in Table 1a:

TABLE 1a

| S. No. | Name of the Material | Qty. | M. Wt. | mmol | Mole Ratio |
|---|---|---|---|---|---|
| 1. | Solketal | 20 g | 132.15 | 151.3 | 1 |
| 2. | Allyl Bromide | 15.7 mL | 120.99 | 166.46 | 1.1 |

TABLE 1a-continued

| S. No. | Name of the Material | Qty. | M. Wt. | mmol | Mole Ratio |
|---|---|---|---|---|---|
| 3. | NaH | 12.1 g | 24 | 302 | 1.99 |
| 4. | MeOH | 10 mL | 32 | — | 0.5 vol. |
| 5. | THF | 200 mL | 72.11 | — | 10 vol. |
| 6. | EtOAc | 3 × 200 mL | 88.11 | — | 3 × 10 vol. |
| 7. | Water | 2 × 200 mL | 18 | — | 2 × 10 vol. |
| 8. | Brine | 200 mL | — | — | 10 vol. |
| 9. | $Na_2SO_4$ | As needed | 142.02 | — | — |

To an ice cold suspension of NaH (60% in oil, 12.1 g, 302 mmol) in THF (200 mL), Solketal (20 g, 151.3 mmol) and allyl bromide (15.7 mL, 166.46 mmol) were sequentially added at 0° C. and stirred at room temperature for 4 h. After the completion of starting material, the reaction mixture was quenched with MeOH (10 mL) and ice, extracted with EtOAc (200 mL×3), washed with $H_2O$ (200 mL×2), brine solution (200 mL×1) and dried over anhy. $Na_2SO_4$. The combined organic extracts were evaporated under reduced pressure to furnish a compound represented by Formula 2 (23 g, 88%) as a pale yellow liquid which was carried to the next step without further purification.

Preparation of a Compound of Formula 3 (3-(allyloxy) propane-1,2-diol)

The compound of Formula 2 obtained above was deprotected to obtain a compound represented by Formula 3. The yield of the compound obtained in this reaction step was 97%. The reaction scheme involved in this process is as follows:

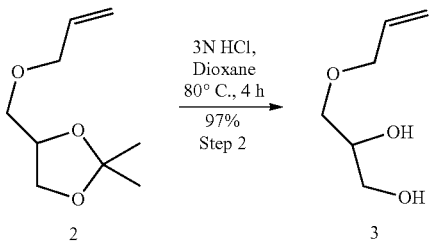

In an exemplary embodiment, the raw materials used for this step are illustrated in Table 2a:

TABLE 2a

| S. No. | Name of the Material | Qty. | M. Wt. | mmol | Mole Ratio |
|---|---|---|---|---|---|
| 1. | Compound of Formula 2 | 23 g | 173.06 | 132.9 | 1 |
| 2. | HCl | 69 mL | 36.5 | — | 3 vol. |
| 3. | Toluene | | | | |

To a solution of compound 2 (23 g, 132.9 mmol) in 3N aq. HCl (69 mL) was added and stirred at 80° C. for 4 h. After completion of starting material, the reaction mixture was cooled and co-distilled with toluene. The combined organic extracts were evaporated under reduced pressure to obtain the crude product which was purified by column chromatography (100-200 mesh silica gel, eluent 3% MeOH-EtOAc to furnish compound 3 (17 g, 97%) as a colorless liquid.

Preparation of a Compound of Formula 4 (5-(allyloxymethyl)-2,2,3,3,8,8,9,9-octamethyl-4,7-dioxa-3,8-disiladecane)

The diol of the compound of Formula 3 obtained above was protected as a TBDMS ether to obtain a compound represented by Formula 4. The yield of the compound obtained in this reaction step was 84%. The reaction scheme involved in this process is as follows:

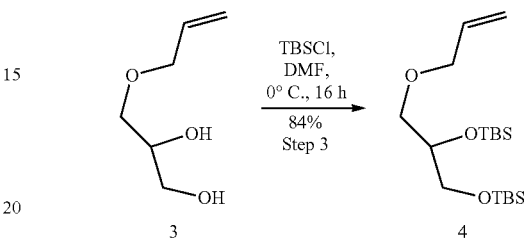

In an exemplary embodiment, the raw materials used for this step are illustrated in Table 3a:

TABLE 3a

| S. No. | Name of the Material | Qty. | M. Wt. | mmol | Mole Ratio |
|---|---|---|---|---|---|
| 1. | Compound of Formula 3 | 3.8 g | 132.4 | 28.7 | 1 |
| 2. | DMF | 30 mL | 73.09 | — | 7.9 vol. |
| 3. | Imidazole | 5.87 g | 68.05 | 86.25 | 3 |
| 4. | TBDMSCl | 13 g | 150.72 | 86.25 | 3 |
| 5. | Ether | 3 × 200 mL | | | 3 × 52.62 vol. |
| 6. | Water | 2 × 200 mL | 18 | — | 2 × 52.62 vol. |
| 7. | Brine | 200 mL | — | — | 52.62 vol. |
| 8. | $Na_2SO_4$ | As needed | 142.02 | — | — |

To a solution of the compound represented by Formula 3 (3.8 g, 28.7 mmol) in DMF (30 mL), Im (5.87 g, 86.25 mmol) and TBDMSCl (13 g, 86.25 mmol) were added sequentially at 0° C. and stirred at room temperature for 16 h. After completion of starting material, the reaction mixture was extracted with ether (200 mL×3), washed with water (200 mL×2), brine (200 mL×1) and dried over anhy. $Na_2SO_4$. The combined organic extracts were evaporated under reduced pressure to obtain the crude product which was purified by column chromatography (100-200 mesh silica gel, eluent hexane) to furnish compound represented by Formula 4 (8.7 g, 84%) as a colorless liquid.

Preparation of a Compound of Formula 5 (5-(allyloxymethyl)-2,2,3,3,8,8,9,9-octamethyl-4,7-dioxa-3,8-disiladecane)

The compound represented by Formula 4 was reacted with iodotridecane in the presence of sec-BuLi to produce a compound represented by Formula 5. The yield of the compound obtained in this reaction step was 37%. The reaction scheme involved in this process is as follows:

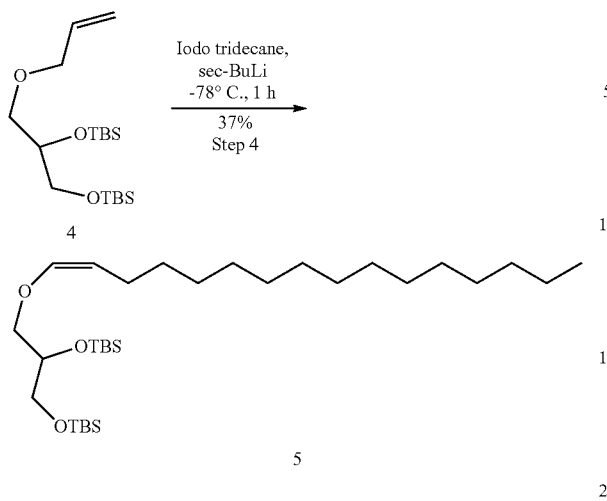

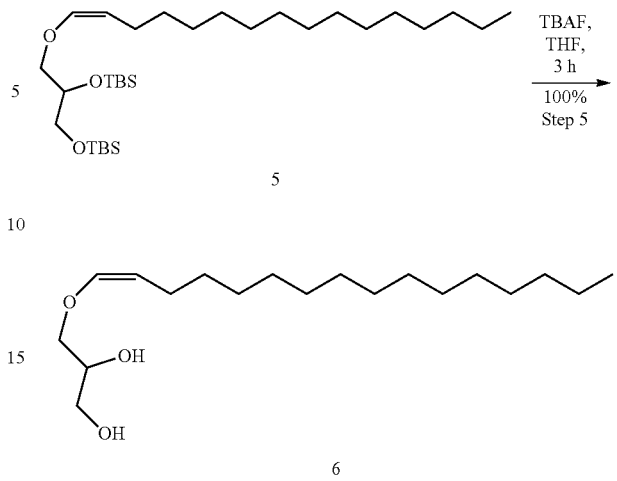

In an exemplary embodiment, the raw materials used for this step are illustrated in Table 4a:

TABLE 4a

| S. No. | Name of the Material | Qty. | M. Wt. | mmol | Mole Ratio |
|---|---|---|---|---|---|
| 1. | Compound of Formula 4 | 1 g | 370.37 | 2.7 | 1 |
| 2. | THF | 25 mL | 72.11 | — | 25 vol. |
| 3. | Sec-BuLi | 2.37 mL | 64.06 | 3.32 | 1.23 |
| 4. | Iodotridecane | 1.03 g | 310.25 | 3.32 | 1.23 |
| 5. | THF | 5 mL | 72.11 | — | 5 vol. |
| 6. | EtOAc | 2 × 200 mL | 88.11 | — | 2 × 200 vol. |
| 7. | Water | 2 × 200 mL | 18 | — | 2 × 200 vol. |
| 8. | Brine | 200 mL | — | — | 200 vol. |
| 9. | $Na_2SO_4$ | As needed | 142.02 | — | — |

To a solution of the compound represented by Formula 4 (1 g, 2.7 mmol) in THF (25 mL), Sec-BuLi (2.37 mL, 3.32 mmol) was added drop wise at −78° C. and stirred for 5 min and iodotridecane (1.03 g, 3.32 mmol) (synthesized in house) in THF (5 mL) was added drop wise and stirred at room temperature for 1 h. After completion of reaction, the reaction mixture was quenched with ice cold water and extracted with EtOAc (200 mL×2) and washed with water (200 mL×2), brine (200 mL×1) and dried over anhy. $Na_2SO_4$. The combined organic extracts were evaporated under reduced pressure to obtain the crude product which was purified by column chromatography (100-200 mesh silica gel, eluent 20% DCM-hexane) to furnish the compound represented by Formula 5 (550 mg, 37%) as a colorless liquid.

Preparation of a Compound of Formula 6 ((Z)-3-(hexadec-1-enyloxy) propane-1,2-diol)

The compound represented by Formula 5 obtained above was deprotected of TDBMS ether to produce a compound of Formula 6. The yield of the compound obtained in this reaction step was 100%. The reaction scheme involved in this process is as follows:

In an exemplary embodiment, the raw materials used for this step are illustrated in Table 5a:

TABLE 5a

| S. No. | Name of the Material | Qty. | M. Wt. | mmol | Mole Ratio |
|---|---|---|---|---|---|
| 1. | Compound of Formula 5 | 3.5 g | 543.48 | 6.44 | 1 |
| 2. | THF | 60 mL | 72.11 | — | 17.14 vol. |
| 3. | TBAF | 25.76 mL | 261.46 | 25.76 | 4 |
| 4. | EtOAc | 2 × 200 mL | 88.11 | — | 2 × 57.14 vol. |
| 5. | Water | 2 × 200 mL | 18 | — | 2 × 57.14 |
| 6. | Brine | 200 mL | — | — | 57.14 |
| 7. | $Na_2SO_4$ | As needed | 142.02 | — | — |

To an ice cold solution of compound represented by Formula 5 (3.5 g, 6.44 mmol) in THF (60 mL), TBAF (25.76 mL, 25.76 mmol) was added drop wise and stirred at room temperature for 3 h. After the completion of starting material, the reaction mixture was quenched with ice and extracted with ethyl acetate (200 mL×2), washed with water (200 mL×2), brine (200 mL×1) and dried over anhy. $Na_2SO_4$. The combined organic extracts were evaporated under reduced pressure to obtain the crude product which was purified by column chromatography (100-200 mesh silica gel, eluent 30% EtOAc-hexane) to furnish the compound represented by Formula 6 (2 g, 100%) as an off white solid.

Preparation of a Compound of Formula 7 ((Z)-1-(tert-butyldimethylsilyloxy)-3-(hexadec-1-enyloxy) propan-2-ol)

Primary alcohol present in the compound represented by Formula 6 was protected with TDBMS to obtain a compound represented by Formula 7. The yield of the compound obtained in this reaction step was 74%. The reaction scheme involved in this process is as follows:

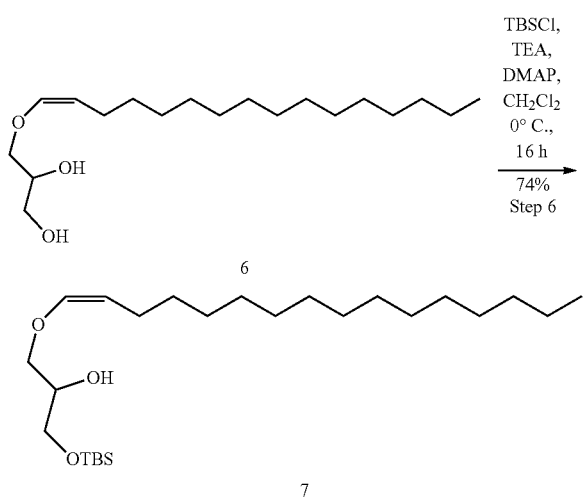

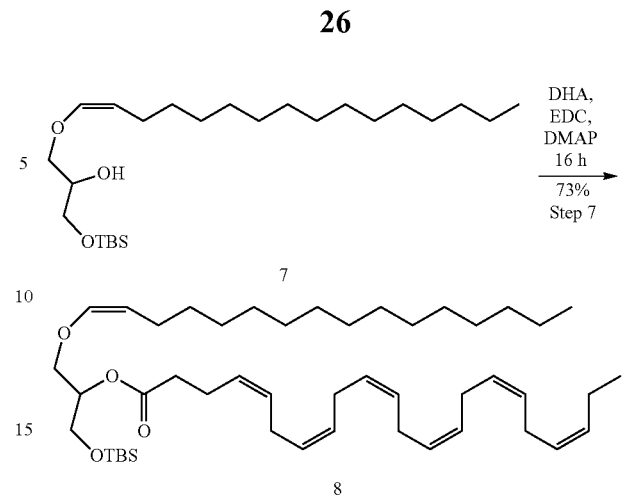

In an exemplary embodiment, the raw materials used for this step are illustrated in Table 6:

TABLE 6

| S. No. | Name of the Material | Qty. | M. Wt. | mmol | Mole Ratio |
|---|---|---|---|---|---|
| 1. | Compound of Formula 6 | 2 g | 314.46 | 6.36 | 1 |
| 2. | DCM | 100 mL | 84.93 | — | 50 vol. |
| 3. | TEA | 2.2 mL | 101.19 | 15.9 | 2.4 |
| 4. | DMAP | 780 mg | 122.17 | 6.36 | 1 |
| 5. | TBDMSCl | 1 g | 143.06 | 6.99 | 1.09 |
| 6. | Dichloromethane | 3 × 100 mL | 84.93 | — | 3 × 50 vol. |
| 7. | Water | 2 × 100 mL | 18 | — | 2 × 50 vol. |
| 8. | Brine | 100 mL | — | — | 50 vol. |
| 9. | $Na_2SO_4$ | As needed | 142.02 | — | — |

To an ice cold solution of the compound represented by Formula 6 (2 g, 6.36 mmol) in DCM (100 mL), TEA (2.2 mL, 15.9 mmol), DMAP (780 mg, 6.36 mmol) and TBDMSCl (1 g, 6.99 mmol) were added sequentially at 0° C. and stirred at room temperature for 16 h. After the completion of starting material, the reaction mixture was quenched with ice and extracted with dichloromethane (100 mL×3), washed with water (100 mL×2), brine (100 mL×1) and dried over anhy. $Na_2SO_4$. The combined organic extracts were evaporated under reduced pressure to obtain the crude product which was purified by column chromatography (100-200 mesh silica gel, eluent 4% EtOAc-hexane) to furnish the compound represented by Formula 7 (2 g, 74%) as a colorless liquid.

Preparation of a Compound of Formula 8 ((4Z,7Z,10Z,13Z,16Z,19Z)-1-(tert-butyldimethylsilyloxy)-3-((Z)-hexadec-1-enyloxy) propan-2-yl docosa-4,7,10,13,16,19-hexaenoate DHA was esterified at the sn2 position of the compound represented by Formula 7 in the presence of EDC.HCL/DMAP to produce a compound represented by Formula 8. The yield of the compound obtained in this reaction step was 73%. The reaction scheme involved in this process is as follows:

In an exemplary embodiment, the raw materials used for this step are illustrated in Table 7a:

TABLE 7a

| S. No. | Name of the Material | Qty. | M. Wt. | mmol | Mole Ratio |
|---|---|---|---|---|---|
| 1. | Compound of Formula 7 | 2 g | 482.26 | 4.67 | 1 |
| 2. | DCM | 100 mL | 84.93 | — | 50 vol. |
| 3. | DHA | 1.68 g | 328.48 | 5.13 | 1.09 |
| 4. | EDC•HCl | 1 g | 191.7 | 5.60 | 1.2 |
| 5. | DMAP | 57 mg | 122.17 | 0.46 | 0.1 |
| 6. | Dichloromethane | 2 × 100 mL | 84.93 | — | 2 × 50 vol. |
| 7. | Water | 2 × 100 mL | 18 | — | 2 × 50 vol. |
| 8. | Brine | 100 mL | — | — | 50 vol. |
| 9. | $Na_2SO_4$ | As needed | 142.02 | — | — |

To an ice cold solution of the compound represented by Formula 7 (2 g, 4.67 mmol) in DCM (100 mL), DHA (1.68 g, 5.13 mmol), EDC.HCl (1 g, 5.60 mmol) and DMAP (57 mg, 0.46 mmol) were added sequentially and stirred at room temperature for 16 h. After the completion of starting materials, the reaction mixture was extracted with DCM (100 mL×2) and washed with water (100 mL×2), brine (100 mL×1) and dried over anhy. $Na_2SO_4$. The combined organic extracts were evaporated under reduced pressure to obtain the crude product which was purified by column chromatography (100-200 mesh silica gel, eluent 4% EtOAc-hexane) to furnish the compound represented by Formula 8 (2.5 gm, 73%) as a pale yellow liquid.

Preparation of a Compound of Formula 9 ((4Z,7Z,10Z,13Z,16Z,19Z)-1-((Z)-hexadec-1-enyloxy)-3-hydroxypropan-2-yl 13 C docosa-4,7,10,13,16,19-hexaenoate)

The compound represented by Formula 8 was deprotected in the presence of excess AcOH to produce a compound represented by Formula 9. The yield of the compound obtained in this reaction step was 95%. The reaction scheme involved in this process is as follows:

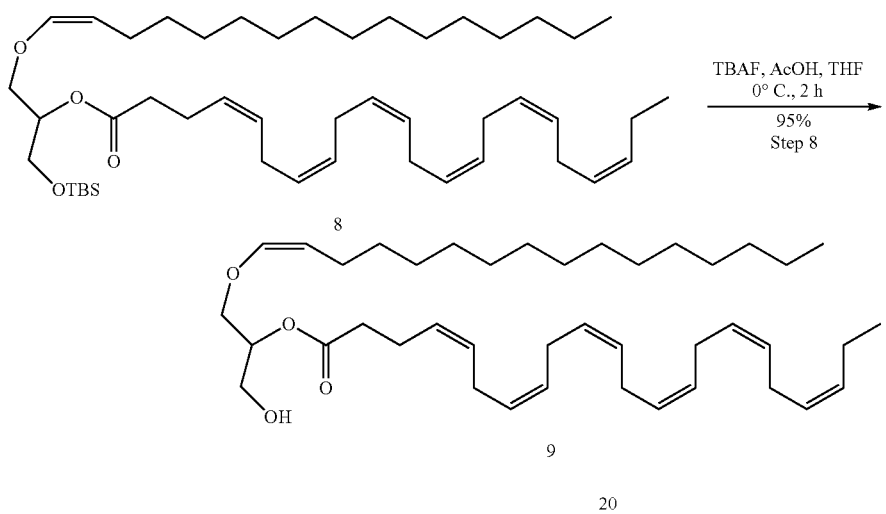

In an exemplary embodiment, the raw materials used for this step are illustrated in Table 8a:

TABLE 8a

| S. No. | Name of the Material | Qty. | M. Wt. | mmol | Mole Ratio |
|---|---|---|---|---|---|
| 1. | Compound of Formula 8 | 2.5 g | 739.64 | 3.38 | 1 |
| 2. | THF | 30 mL | 72.11 | — | 12 vol. |
| 3. | AcOH | 2.02 mL | 60.05 | 33.8 | 10 |
| 4. | TBAF | 10.14 mL | 261.46 | 10.14 | 3 |
| 5. | EtOAc | 2 × 100 mL | 88.11 | — | 2 × 40 vol. |
| 6. | Water | 2 × 100 mL | 18 | — | 2 × 40 vol. |
| 7. | Brine | 100 mL | — | — | 20 vol. |
| 8. | $Na_2SO_4$ | As needed | 142.02 | — | — |

To an ice cold solution of the compound represented by Formula 8 (2.5 g, 3.38 mmol) in THF (30 mL), AcOH (2.02 mL, 33.8 mmol) and TBAF (10.14 mL, 10.14 mmol) were added at 0° C. and stirred at room temperature for 2 h. After the completion of starting materials, the reaction mixture was quenched with ice and extracted with EtOAc (100 mL×2) and washed with water (100 mL×2), brine (100 mL×1) and dried over anhy. $Na_2SO_4$. The combined organic extracts were evaporated under reduced pressure to obtain the crude product which was purified by column chromatography (100-200 mesh silica gel, eluent 30% EtOAc-hexane to furnish the compound represented by Formula 9 (2 gm, 95%) as a pale yellow liquid.

Preparation of a Compound of Formula A

A cyclic phosphoethanolamine group was added to the compound represented by Formula 9 to produce a compound represented by Formula A, using a two step protocol, wherein $POCl_3$ was added to the compound represented by Formula 9 to produce a dichlorophosphate intermediate, which was quenched with ethanolamine to give the cyclic phosphoethanolamine. The yield of the compound obtained in this reaction step was 26%. The reaction scheme involved in this process is as follows:

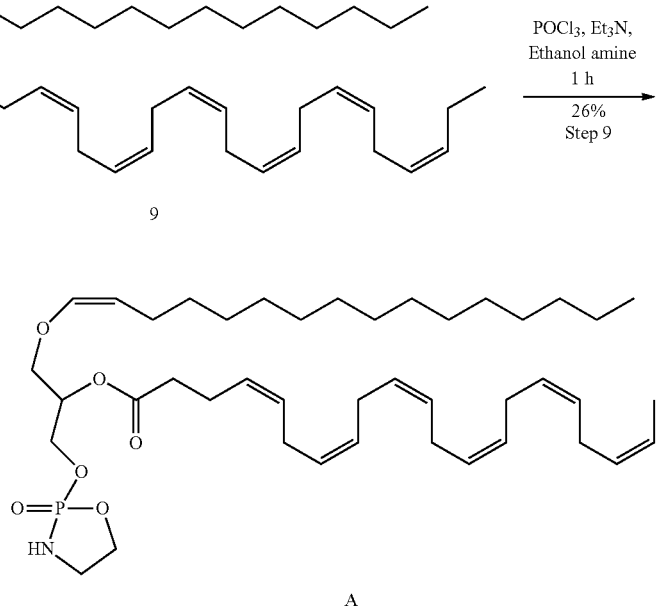

In an exemplary embodiment, the raw materials used for this step are illustrated in Table 9a:

TABLE 9a

| S. No. | Name of the Material | Qty. | | M. Wt. | mmol | Mole Ratio | |
|---|---|---|---|---|---|---|---|
| 1. | Compound of Formula 9 | 70 | mg | 636.36 | 0.11 | 1 | |
| 2. | POCl$_3$ | 0.03 | mL | 153.33 | 0.33 | 3 | |
| 3. | Hexane | 2 | mL | 86.18 | — | 28.57 | |
| 4. | TEA | 0.15 | mL | 101.19 | 1.12 | 10.18 | |
| 5. | Trichloroethylene | 4 | mL | 131.39 | — | 57.14 | vol. |
| 6. | Toluene | 4 | mL | 92.14 | — | 57.14 | vol. |
| 7. | THF | 8 | mL | 72.11 | — | 114.28 | vol. |
| 8. | Ethanolamine | 20.5 | mg | 61.08 | 0.33 | 3 | |
| 9. | TEA | 0.62 | mL | 101.19 | 4.4 | 40 | |
| 10. | THF | 5 | mL | 72.11 | — | 71.42 | vol. |
| 11. | EtOAc | 10 | mL | 88.11 | — | 142.85 | vol. |

To an ice cold solution of POCl$_3$ (0.03 mL, 0.33 mmol) in hexane (2 mL), TEA (0.15 mL, 1.12 mmol), and the compound represented by Formula 9 (70 mg, 0.11 mmol) in trichloroethylene (4 mL) were added at 0° C. drop wise and stirred for 30 min and 1 h at room temperature. The reaction mixture was filtered through a small Celite™ pad, washed with toluene (4 mL) and the filtrate was evaporated under reduced pressure.

The crude material obtained was dissolved in THF (8 mL) ethanolamine (20.5 mg, 0.33 mmol) and TEA (0.62 mL, 4.4 mmol) in THF (5 mL) were added at 0° C. drop wise to the reaction mixture and stirred at room temperature for 30 min. The reaction mixture was filtered through a Celite™ pad and washed with EtOAc (10 mL). The combined organic extracts were evaporated under reduced pressure to obtain the crude product which was purified by column chromatography (100-200 mesh silica gel, eluent 60% EtOAc-hexane) to furnish the compound represented by Formula A (22 mg, 26%) as a colorless liquid.

Example 3

Conversion of a Compound of Formula A to a Compound of Formula B

In a preferred embodiment of the invention, a one step synthetic process is provided for conversion of a compound represented by Formula A as obtained above to a compound represented by Formula B. An example of this method is described in detail below.

Preparation of a Compound of Formula B

A compound of Formula A as obtained above, comprising a cyclic phosphoethanolamine, was converted to a compound represented by Formula B in the presence of THF and H$_2$O. The reaction scheme involved in this process is as follows:

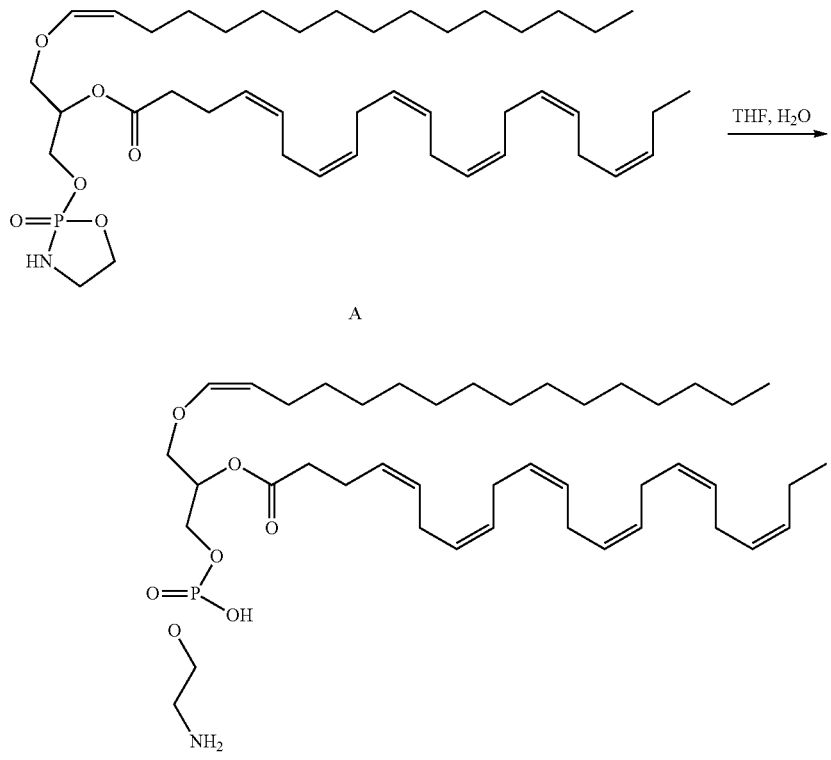

In an exemplary embodiment of this step, the compound represented by Formula A was dissolved in THF and stirred with water overnight, and we expect the disappearance of one of the two peaks in our analysis. As expected, HPLC and LCMS analysis indicated a single peak at retention time 17.44, with the mass 748 corresponding to the compound represented by Formula B. However, LCMS analysis of the compound of Formula B sample which was stirred with a drop of acetic acid was not clean suggesting decomposition of the product in acidic medium.

The preferred embodiments of the invention described above are merely exemplary of the invention, which can be embodied in various forms. Therefore, specific details relating to the reagents and reaction conditions disclosed herein are not to be interpreted as limiting, but merely as an example. It will be apparent to a person skilled in the art that a number of variations and modifications can be made without departing from the scope of the invention as defined in the claims.

What is claimed is:

1. A process of preparing a compound represented by

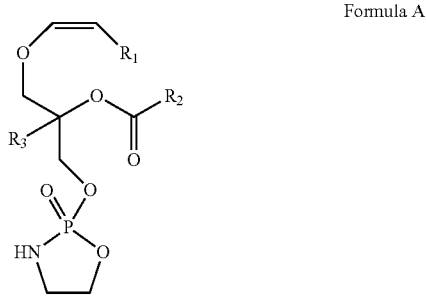

Formula A wherein $R_1$ and $R_2$ are the same or different saturated, unsaturated, or polyunsaturated $C_1$-$C_{28}$ hydrocarbon chains, and optionally derived from fatty acids; and $R_3$ is hydrogen or a $C_1$-$C_3$ alkyl group, the process comprising:

a) coupling a solketel represented by Formula 1:

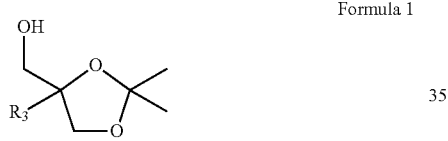

Formula 1 with an allyl halide to obtain a compound represented by Formula 2:

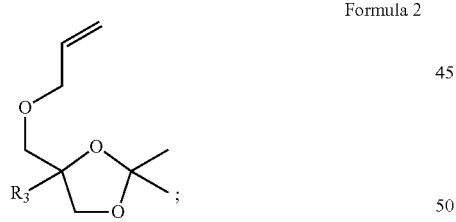

Formula 2 b) deprotecting the ketal present in the compound represented by Formula 2 to obtain a compound represented by Formula 3:

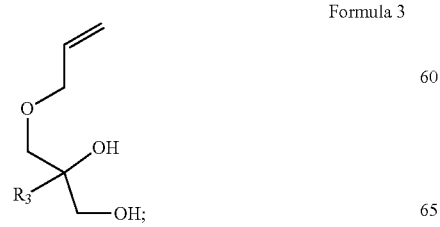

Formula 3 c) protecting the diol present in the compound represented by Formula 3 to obtain a compound represented by Formula (iv):

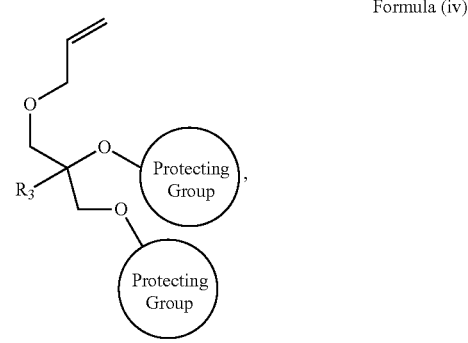

Formula (iv)

d) reacting a compound as represented by the formula X—$R_1$ with the compound represented by Formula (iv) to obtain a compound represented by Formula (v)

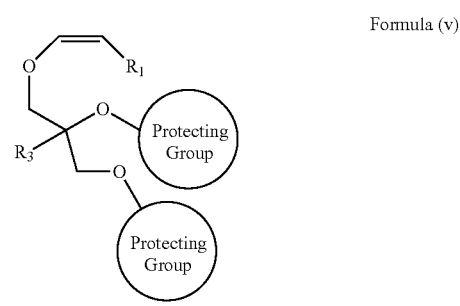

Formula (v)

wherein $R_1$ is as defined above and X is a halogen, e) deprotecting the ether groups present in the compound represented by Formula (v) to obtain a compound represented by Formula 6:

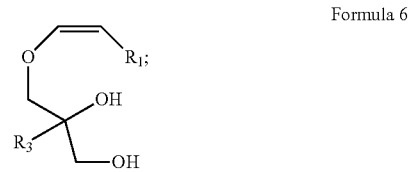

Formula 6 f) protecting the primary alcohol present in the compound represented by Formula 6 to yield a compound represented by Formula (vii):

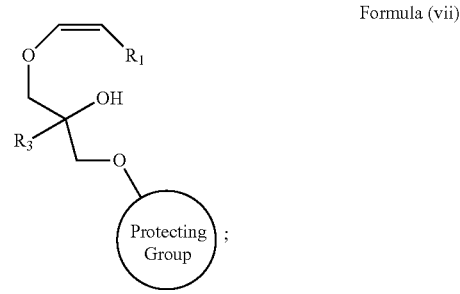

Formula (vii)

g) esterifying a fatty acid as represented by $R_2$—COOH to the compound represented by Formula (vii) to obtain a compound represented by Formula (viii):

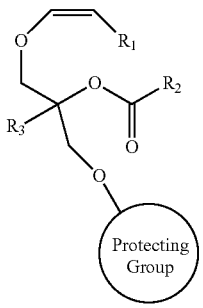

Formula (viii)

wherein $R_2$ is as defined above, h) deprotecting the ether present in the compound represented by Formula (viii) to obtain a compound represented by Formula 9

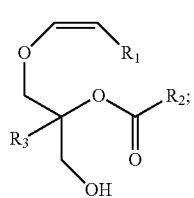

Formula 9 and reacting $POCl_3$ with the compound represented by Formula 9, ethanolamine, and triethanolamine (TEA) to yield the compound represented by Formula A.

2. The process as claimed in claim 1 wherein $R_1$, $R_2$ or both $R_1$ and $R_2$ are $C_1$-$C_{28}$ alkyl chains comprising up to 6 double bonds.

3. The process as claimed in claim 1 wherein $R_1$ is a $C_1$-$C_{20}$ alkyl group.

4. The process as claimed in claim 1 wherein $R_2$ is a $C_2$-$C_{28}$ alkenyl group with 1 to 6 double bonds.

5. The process as claimed in claim 1 wherein $R_3$ is hydrogen.

6. The process as claimed in claim 1 wherein the allyl halide is allyl bromide.

7. The process as claimed in claim 1 wherein diol present in the compound represented by Formula 3 is protected with a tert-butyldimethylsilyl (TBS) group.

8. The process as claimed in claim 1 wherein X in $XR_1$ is Cl, Br, F or I.

9. The process as claimed in claim 1 wherein X in $XR_1$ is I.

10. The process as claimed in claim 1 wherein the primary alcohol present in the compound represented by Formula 6 is protected with a tert-butyldimethylsilyl (TBS) group.

11. The process as claimed in claim 1 wherein the compound as represented by X—$R_1$ in step (d) is iodotridecane.

12. The process as claimed in claim 1 wherein the fatty acid as represented by $R_2$—COOH in step (g) is docosahexanoic acid (DHA).

13. The process as claimed in claim 11 wherein the iodotridecane is chemically synthesized.

14. The process as claimed in claim 12 wherein the DHA is chemically synthesized.

15. The process as claimed in claim 1, wherein the coupling reaction of step (a) is carried out in the presence of NaH, tetrahydrofuran (THF) and allyl bromide.

16. The process as claimed in claim 15, wherein the coupling reaction of step (a) is carried out at a temperature of between about 0° C. to about room temperature.

17. The process as claimed in claim 1, wherein the deprotecting reaction of step (b) is conducted under acidic conditions in the presence of HCl.

18. The process as claimed in claim 17, wherein the deprotecting reaction of step (b) is carried out at a temperature of about 80° C.

19. The process as claimed in claim 1, wherein the protection reaction of step (c) comprises reacting the compound represented by Formula 3 with a tert-butyldimethylsilyl chloride (TBDMSC1) in the presence of dimethylformamide (DMF) and imidazole.

20. The process as claimed in claim 19, wherein the protection reaction of step (c) is carried out at about room temperature.

21. The process as claimed in claim 1, wherein the step (d) comprises reacting a haloalkane dissolved in tetrahydrofuran (THF) with the compound represented by Formula (iv) in the presence of THF and sec-BuLi.

22. The process as claimed in claim 21, wherein the coupling reaction of step (d) is carried out at a temperature of between about −78° C. to about room temperature.

23. The process as claimed in claim 22, wherein the haloalkane as represented by X—$R_1$ is iodotridecane.

24. The process as claimed in claim 23, wherein the compound formed in step (d) is an α alkylated compound represented by Formula (v).

25. The process as claimed in claim 1, wherein the deprotection reaction of step (e) is carried out in the presence of tetrahydrofuran (THF) and tetra-n-butylammonium fluoride (TBAF).

26. The process as claimed in claim 25, wherein the deprotection reaction of step (e) is carried out at a temperature of between about 0° C. to about room temperature.

27. The process as claimed in claim 1, wherein the protection reaction of step (f) comprises reacting tert-butyldimethylsilyl chloride (TBDMSC1) with the compound represented by Formula 6 in the presence of dichloromethane (DCM), triethanolamine (TEA) and 4-Dimethylaminopyridine (DMAP).

28. The process as claimed in claim 27, wherein the protection reaction of step (f) is carried out at a temperature of between about 0° C. to about room temperature.

29. The process as claimed in claim 1, wherein the esterification reaction of step (g) is carried out in the presence of dichloromethane (DCM), 1-ethyl-3-(3-dimethyllaminopropyl)carbodiimide hydrochloride (EDC.HCl) and 4-dimethylaminopyridine (DMAP).

30. The process as claimed in claim 29, wherein the esterification reaction of step (g) is carried out at a temperature of between about 0° C. to about room temperature.

31. The process as claimed in claim 30 wherein the fatty acid as represented by $R_2$—COOH is docosahexanoic acid (DHA).

32. The process as claimed in claim 1, wherein the deprotection reaction of step (h) is carried out in the presence of tetrahydrofuran (THF), AcOH and tetra-n-butylammonium fluoride (TBAF).

33. The process as claimed in claim 32, wherein the deprotection reaction of step (h) is carried out at between about 0° C. to about room temperature.

34. The process as claimed in claim 1, wherein the step (i) comprises:

a). reacting POCl$_3$ with the compound represented by Formula 9 dissolved in trichloroethylene in the presence of hexane and triethanolamine (TEA) to yield a crude material;

b). dissolving the crude material in tetrahydrofuran (THF) forming a reaction mixture; and c). adding ethanolamine and TEA in THF to the reaction mixture to yield the compound represented by Formula A.

35. The process as claimed in claim 34, wherein the step (i) is carried out at a temperature of between about 0° C. to about room temperature.

36. The process as claimed in claim 1 wherein the compound represented by Formula A which is obtained is:

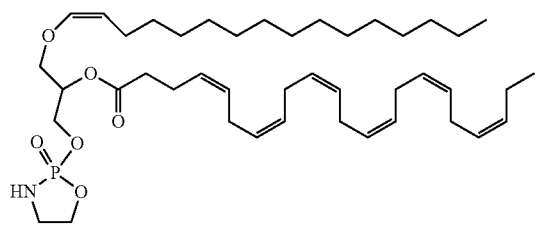

Formula A'

37. A process of converting a compound represented by Formula A:

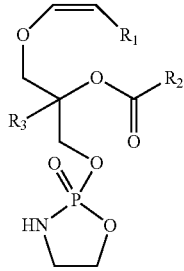

Formula A wherein R$_1$ and R$_2$ are the same or different saturated, unsaturated, or polyunsaturated C$_1$-C$_{28}$ hydrocarbon chains, and optionally derived from fatty acids; and R$_3$ is hydrogen or a C$_1$-C$_3$ alkyl group, the process comprising converting the compound represented by Formula A to a compound represented by Formula B:

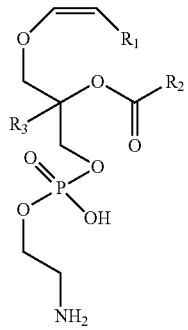

Formula B the conversion process being carried out in the presence of tetrahydrofuran (THF) and H$_2$O.

38. The process as claimed in claim 37 wherein the compound represented by Formula A is

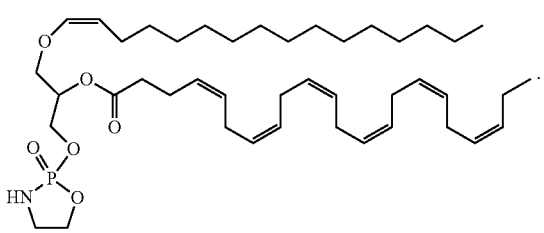

Formula A'

39. The compound of Formula A:

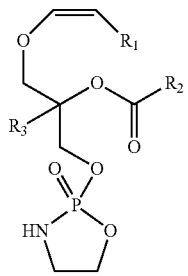

Formula A wherein R$_1$ and R$_2$ are the same or different saturated, unsaturated, or polyunsaturated C$_1$-C$_{28}$ hydrocarbon chains, and optionally derived from fatty acids; and R$_3$ is hydrogen or a C$_1$-C$_3$ alkyl group, prepared by the process as claimed in claim 1.

* * * * *

UNITED STATES PATENT AND TRADEMARK OFFICE
CERTIFICATE OF CORRECTION

PATENT NO. : 9,169,280 B2
APPLICATION NO. : 14/359098
DATED : October 27, 2015
INVENTOR(S) : M. Amin Khan, Paul L. Wood and Dayan Goodenowe Page 1 of 1

It is certified that error appears in the above-identified patent and that said Letters Patent is hereby corrected as shown below:

In the claims

In claim 1, at column 31, line 10, insert --Formula A-- after "represented by".

In claim 29, at column 34, lines 52-53, delete "1-ethyl-3-(3-dimethyllaminopropyl)carbodiimide" and insert in its place --1-ethyl-3-(3-dimethylaminopropyl)carbodiimide--.

Signed and Sealed this
Nineteenth Day of July, 2016

Michelle K. Lee
*Director of the United States Patent and Trademark Office*